(12) United States Patent
Janbakhsh et al.

(10) Patent No.: US 7,823,589 B2
(45) Date of Patent: Nov. 2, 2010

(54) BALL JOINT FOR A MASK APPARATUS FOR USE IN A BREATHING ASSISTANCE SYSTEM

(75) Inventors: Mahmoud Janbakhsh, San Ramon, CA (US); Mark Jacobus Van Kerkwyk, Fremont, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 999 days.

(21) Appl. No.: 11/533,062

(22) Filed: Sep. 19, 2006

(65) Prior Publication Data

US 2008/0072910 A1  Mar. 27, 2008

(51) Int. Cl.
  *A62B 18/08*  (2006.01)
  *A62B 18/02*  (2006.01)
  *A62B 9/04*  (2006.01)
  *A62B 9/00*  (2006.01)

(52) U.S. Cl. ............... 128/206.24; 128/206.21; 128/200.24; 128/202.27

(58) Field of Classification Search ............ 128/203.29, 128/205.25, 206.21, 206.27, 206.28, 207.11, 128/207.13, 206.12
See application file for complete search history.

(56) References Cited

U.S. PATENT DOCUMENTS

| | | | | |
|---|---|---|---|---|
| 4,938,209 A * | 7/1990 | Fry | | 128/200.21 |
| 5,921,239 A | 7/1999 | McCall et al. | | 128/205.25 |
| 6,209,542 B1 | 4/2001 | Thornton | | 128/206.29 |
| 6,467,483 B1 | 10/2002 | Kopacko et al. | | 128/207.12 |
| 6,532,961 B1 | 3/2003 | Kwok et al. | | 128/206.21 |
| 6,810,849 B1 | 11/2004 | Hirsch et al. | | 123/185.3 |
| 6,823,869 B2 | 11/2004 | Raje et al. | | 128/206.24 |
| 6,926,004 B2 | 8/2005 | Schumacher | | 128/206.27 |
| 7,549,422 B2 * | 6/2009 | Frerichs et al. | | 128/207.11 |
| 2003/0221691 A1 | 12/2003 | Biener et al. | | 128/206.24 |
| 2004/0211415 A1 | 10/2004 | Lurie | | 128/203.11 |

(Continued)

FOREIGN PATENT DOCUMENTS

EP    1 555 039 A    7/2005

(Continued)

OTHER PUBLICATIONS

International Search Report and Written Opinion PCT/US2007/078722, 17 pages, Apr. 7, 2008.

(Continued)

*Primary Examiner*—Justine R Yu
*Assistant Examiner*—Rachel T Young

(57) ABSTRACT

A mask apparatus for use in a breathing assistance system may include a ball joint at least partially defined by a housing, a ball member, and a mounting system. The housing may be configured to support a cushion configured to provide a seal against a patient's face. The housing may include a first side defining a first housing opening, and a second side configured to face the cushion and defining a second housing opening. The ball member may be positioned in the first housing opening and may define a ball member opening configured for communicating gas though the first housing opening. The mounting system may be configured to secure the ball member in the first housing opening such that the housing, the ball member, and the mounting system define a ball joint allowing the ball member to rotate about multiple axes relative to the housing and the mounting system.

19 Claims, 6 Drawing Sheets

U.S. PATENT DOCUMENTS

| | | | |
|---|---|---|---|
| 2004/0211427 A1 | 10/2004 | Jones, Jr. et al. | 128/206.27 |
| 2005/0005940 A1 | 1/2005 | Gunaratnam | 128/206.27 |
| 2005/0150497 A1 | 7/2005 | Eifler et al. | 128/206.21 |
| 2005/0155603 A1 | 7/2005 | Frerichs et al. | 128/206.21 |
| 2006/0283460 A1* | 12/2006 | Brown et al. | 128/206.24 |
| 2008/0066745 A1 | 3/2008 | Janbakhsh et al. | 128/200.24 |
| 2008/0066755 A1 | 3/2008 | Janbakhsh et al. | 128/205.25 |
| 2008/0210241 A1 | 9/2008 | Schulz et al. | 128/206.21 |

FOREIGN PATENT DOCUMENTS

| | | |
|---|---|---|
| EP | 1 632 262 A | 3/2006 |
| WO | 2005028011 A | 3/2005 |
| WO | WO 2005/028011 A | 3/2005 |
| WO | WO 2006024288 A2 * | 3/2006 |

OTHER PUBLICATIONS

International Search Report with Written Opinion PCT/US2007/078726, 12 pages.

International Search Report, PCT/US2007/078722, 6 pages, mailed on Jul. 4, 2008.

Beall, Glenn, "By Design: Polypropylene Part Design, Part 2-Living Hinges", IMM Magazine Article Archive, 2 pages.

* cited by examiner

BALL JOINT FOR A MASK APPARATUS FOR USE IN A BREATHING ASSISTANCE SYSTEM

TECHNICAL FIELD

The present disclosure relates generally to the field of breathing assistance systems, e.g., a ball joint for a mask apparatus for use in a breathing assistance system.

BACKGROUND

In recent years, continuous positive airway pressure (CPAP) therapy has become a common prescription for individuals suffering from sleep apnea and/or other breathing ailments. Such therapy may involve placement of a nose or face mask on the subject during sleeping, while positive pressure air is continuously delivered to the subject through the mask. The positive pressure air may be delivered to the patient's upper airway via a face mask or other patient interface in order to prevent the upper airway tissues from collapsing during sleep, thus reducing the occurrence and/or severity of sleep apnea.

SUMMARY

In accordance with one embodiment of the disclosure, a mask apparatus for use in a breathing assistance system may include a ball joint at least partially defined by a housing, a ball member, and a mounting system. The housing may be configured to support a cushion configured to provide a seal against a patient's face. The housing may include a first side defining a first housing opening, and a second side configured to face the cushion and defining a second housing opening. The ball member may be positioned in the first housing opening and may define a ball member opening configured for communicating gas though the first housing opening. The mounting system may be configured to secure the ball member in the first housing opening such that the housing, the ball member, and the mounting system define a ball joint allowing the ball member to rotate about multiple axes relative to the housing and the mounting system.

In accordance with another embodiment of the disclosure, a breathing assistance system may include a gas delivery apparatus configured to deliver gas toward a patient, a mask apparatus in fluid communication with the gas delivery apparatus, and a connection system configured to communicate gas from the gas delivery apparatus to the mask apparatus. The mask apparatus may include a housing, a ball member, and a mounting system. The housing may be configured to support a cushion configured to provide a seal against a patient's face. The housing may include a first side defining a first housing opening, and a second side configured to face the cushion and defining a second housing opening. The ball member may be positioned in the first housing opening and may define a ball member opening configured for communicating gas though the first housing opening. The mounting system may be configured to secure the ball member in the first housing opening such that the housing, the ball member, and the mounting system define a ball joint allowing the ball member to rotate about multiple axes relative to the housing and the mounting system.

In accordance with another embodiment of the disclosure, a ball joint for a mask apparatus for use in a breathing assistance system. The ball joint may include a ball member secured between a mounting system and a housing configured to support a cushion for providing a seal against a patient's face. The ball member may be secured in a housing opening defined in the housing, and may be configured to rotate about multiple axes relative to the housing and the mounting system. The ball member may define a ball member opening configured for communicating gas from a gas delivery conduit toward the patient though the first housing opening.

In accordance with another embodiment of the disclosure, a method for assembling a mask apparatus for use in a breathing assistance system may include positioning a ball member in a housing opening defined in a housing configured to support a cushion for providing a seal against a patient's face, the ball member defining a ball member opening configured for communicating gas though the housing opening. the method may further include attaching a mounting system to the housing to secure the ball member in the housing opening such that the housing, the ball member, and the mounting system define a ball joint allowing the ball member to rotate about multiple axes relative to the housing and the mounting system.

In accordance with another embodiment of the disclosure, a mask apparatus for use in a breathing assistance system may include housing means, ball means, and mounting means. The housing means may be configured for supporting a cushion configured to provide a seal against a patient's face, and may have a first side and a second side, the first side defining a first housing means opening, and the second side configured to face the cushion and defining a second housing means opening. The ball means may be positioned in the first housing means opening, and may define a ball means opening configured for communicating gas though the first housing means opening. The mounting means may be configured for securing the ball means in the first housing means opening such that the housing means, the ball means, and the mounting means define a ball joint allowing the ball means to rotate about multiple axes relative to the housing means and the mounting means.

BRIEF DESCRIPTION OF THE DRAWINGS

FIG. 5 also illustrates an adjustment arm of an adjustment system releasably locked with a locking member of the adjustment system;

DETAILED DESCRIPTION OF THE DRAWING

Figure 1:
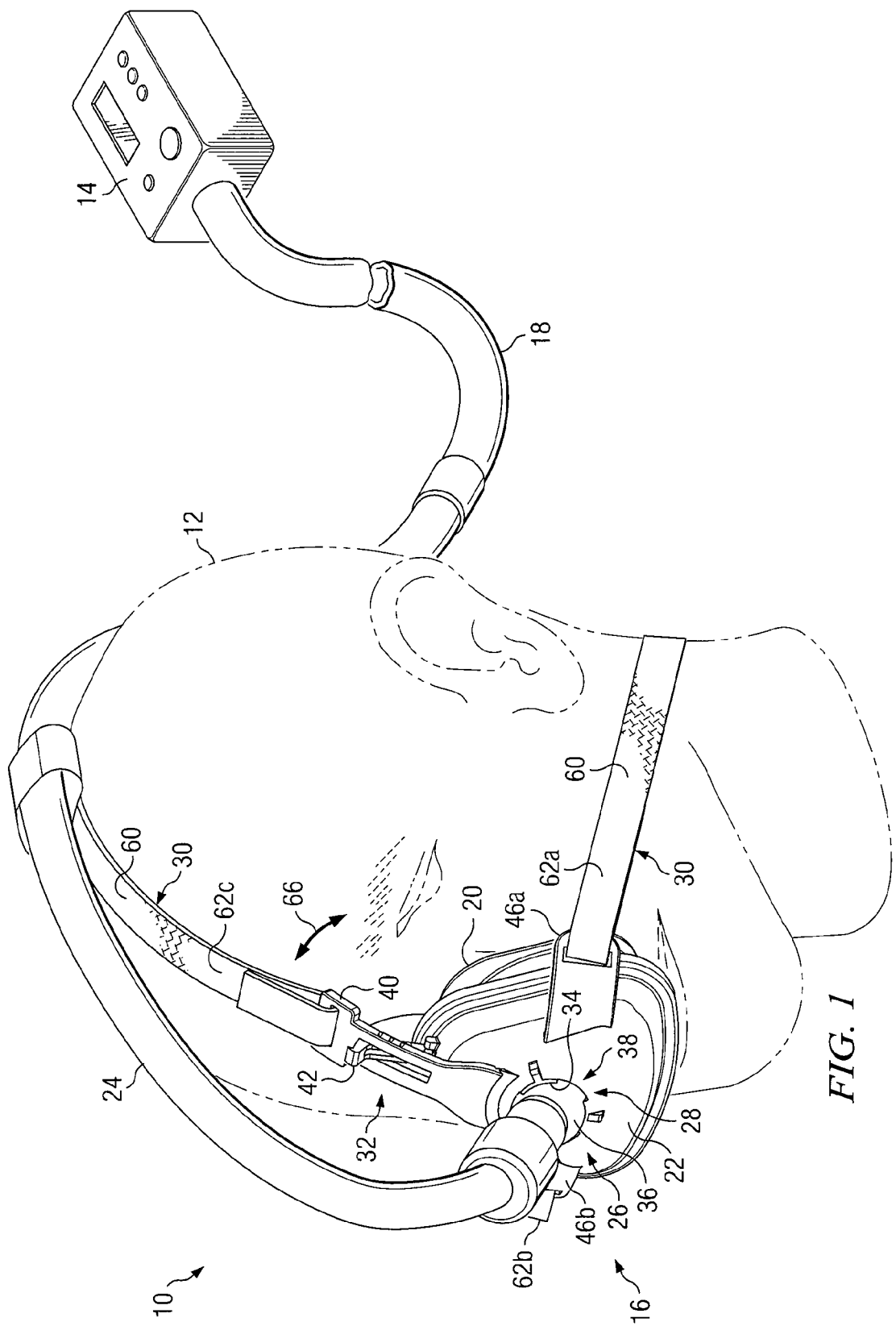
FIG. 1 illustrates an example breathing assistance system for providing breathing assistance to a patient, according to one embodiment of the disclosure.

Selected embodiments of the disclosure may be understood by reference, in part, to FIGS. 1-7D, wherein like numbers refer to same and like parts. The present disclosure relates generally to mask apparatuses for breathing assistance systems (e.g., ventilators, CPAP devices, or BiPAP devices).

In some embodiments, a mask apparatus may include a cushion for providing a seal against a patient's face, a housing configured to support the cushion, and a ball joint disposed in the housing that allows multi-axial rotation of a gas delivery conduit relative to the housing. The gas delivery conduit may be configured to deliver gas through the housing for delivery to the patient. The ball joint may include a ball member positioned in an opening formed in the housing, and a mounting system configured to secure the ball member in the housing opening such that the housing, the ball member, and the mounting system define a ball joint allowing the ball member to rotate about multiple axes relative to the housing and the mounting system. The ball member may have a passageway extending therethrough for communicating gas from the gas delivery conduit into the housing and toward the patient.

In some embodiments including a ball joint, a gas exhaust system may be defined by or associated with the ball joint. For example, one or more exhaust passageways may be defined between an outer surface of the ball member and the housing opening, wherein the one or more exhaust passageways are configured for communicating exhaust gas away from the patient.

In some embodiments, a mask apparatus may include a cushion for providing a seal against a patient's face, a housing configured to support the cushion, and an adjustment system supported by the housing and configured to adjust the fit of the mask apparatus (e.g., the cushion) against the face. For example, the adjustment system may include an adjustment arm that interrelates with a locking member to adjust and/or lock the angle of the adjustment arm relative to the housing. The adjustment arm may be rotatably coupled to the housing at a first end and may be coupled to a head gear (e.g., a head strap) at a second, free end. The adjustment arm may rotate relative to the housing to adjust a distance between the free end of the adjustment arm and the patient's head (e.g., proximate the forehead). The locking member may be coupled to the housing and may be configured to secure the adjustment arm in one of a plurality of predetermined rotational positions with respect to the housing.

A mask apparatus according to the present disclosure may include any one, some, or all of such features. For example, a mask apparatus may include a ball joint, an exhaust system associated with the ball joint, and an adjustment system. As another example, a mask apparatus may include a ball joint, an exhaust system associated with the ball joint, but no adjustment system. As another example, a mask apparatus may include a ball joint, an adjustment system, and an exhaust system unrelated to the ball joint. As another example, a mask apparatus may include an adjustment system, but not ball joint.

FIG. 1 illustrates an example breathing assistance system 10, according to one embodiment of the disclosure. Breathing assistance system 10 may be generally configured to provide breathing assistance (e.g., providing ventilation and/or treating an apnea or other breathing condition) to a patient 12. Breathing assistance system 10 may include a gas delivery system 14, a mask apparatus 16, and a connection system 18 between gas delivery system 14 and mask apparatus 16.

Gas delivery system 14 may include any device or devices configured to generate, supply, and/or deliver gas (e.g., pressurized air) toward patient 12 via mask apparatus 16. For example, gas delivery system 14 may comprise a device capable of generating pressurized air (e.g., a ventilator, CPAP system, or BiPAP system), a wall outlet through which pressurized air may be supplied (e.g., in a hospital or clinic), one or more tanks of compressed gas, a compressor, or any other suitable source of pressurized or non-pressurized gas. As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example. The term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Mask apparatus 16 may be generally configured to deliver gas supplied by gas delivery system 14 to patient 12 and/or to communicate exhaust gas away from patient 12. In various embodiments, mask apparatus 16 may include one, some or all of the following features:

(a) a cushion 20 configured to provide a seal against the patient's face (e.g., around the patient's nose and/or mouth);

(b) a housing 22 configured to support cushion 20;

(c) a gas delivery conduit 24 configured to communicate gas from gas delivery system toward cushion 20;

(d) a ball joint 26 configured to provide a flexible, movable, and/or adjustable connection between housing 22 and gas delivery conduit 24;

(e) a gas exhaust system 28 configured to remove exhaled gas away from patient 12;

(f) a headgear 30 configured to secure mask apparatus 16 on the patient's head and/or to secure cushion 20 against the patient's face; and/or (g) an adjustment system 32 for adjusting the fit of mask apparatus 16 against the patient's head (e.g., for adjusting the fit of cushion 20 against the patient's face).

Mask apparatus 16 may also include any other suitable components, e.g., a forehead cushion or other forehead support system, one or more additional adjustment systems, connection members, and/or conduits for communicating gas toward and/or away from patient 12.

Mask apparatus 16 may be coupled to gas delivery system 14 by connection system 18. Connection system 18 may include any one or more conduits (e.g., one or more flexible hoses and/or rigid conduits) for communicating gas from gas delivery system 14 to mask apparatus 16. In some embodiments, connection system 18 may be coupled to delivery conduits 24 of mask apparatus 16. When assembled, breathing assistance system 10 may define one or more gas delivery passageways from gas delivery system 14 to patient 12, passing through connection system 18, mask apparatus 16, and/or one or more other components of system 10. Such passageways may be used to deliver gas from gas delivery system 14 to patient 12. In addition, in some embodiments, mask apparatus 16 and/or connection system 18 may include or define one or more passageways for communicating exhaled gas away from patient 12.

Cushion 20 may comprise any structure suitable for contacting and/or providing a seal against a patient's face. In some embodiments, cushion 20 may be configured to surround, cover, or interface with the nose and/or the mouth. For example, cushion 20 may comprise a nasal cushion configured to fit around the nose, a mouth cushion configured to fit around the mouth, a face cushion configured to fit around both the nose and mouth, or nasal pillows configured to directly interface with the nostrils.

Cushion 20 may be formed from any suitable materials, e.g., materials suitable for forming a seal with the patient's face. In some embodiments, cushion 20 may be formed from relatively flexible or deformable materials, such as flexible or deformable plastic, rubber, polymer, silicon, or gel, for example. In some embodiments, cushion 20 may have one or more membranes which may be contoured to provide a seal against the patient's face. In other embodiments, cushion 20 may include one or more inflatable portions. Cushion 20 may have any suitable shape and/or cross-section. In some embodiments in which cushion 20 is configured to fit around the patient's nose (e.g., as shown in FIG. 1), cushion 20 may have a generally triangular shape.

Housing 22 may comprise any one or more components of mask apparatus 16 configured to support (directly or indirectly) cushion 20. For example, housing 22 may comprise a shell structure, a support member, a frame member, a base member, a connection member, an arm member, or a conduit. In the example embodiment shown in FIG. 1, housing 22 comprises a mask shell or frame to which cushion 20 is directly attached.

In addition, housing 22 may house or form a portion of ball joint 26. As discussed below with reference to FIG. 2, housing may define an opening 34 in which a ball member 36 may be positioned such that ball member 36 may rotate about multiple axes relative to housing 22.

In addition, housing 22 may provide or help define gas exhaust system 28. For example, as discussed below with reference to FIGS. 2 and 6A-6B, one or more exhaust passageways 38 may be defined between opening 34 of housing 22 and an outer surface of ball member 36. Such exhaust passageways 38 may be configured to communicate exhaust gas from patient 12 (e.g., $CO_2$) away from patient 12.

In addition, housing 22 may support (directly or indirectly) adjustment system 32 for adjusting the fit of mask apparatus 16 against the patient's head (e.g., for adjusting the fit of cushion 20 against the patient's face). In the embodiment shown in FIG. 1, adjustment system 32 may include an adjustment arm 40 and a locking member 42 supported by housing 22, which may interact in order to adjust the distance between a free end of adjustment arm 40 and the patient's head.

In addition to supporting adjustment system 32 that is coupled to headgear 30, housing 22 may be further configured to support headgear 30. For example, housing 22 may include one or more headgear attachment members 46 for securing headgear 30. In the illustrated embodiment, housing 22 includes a headgear attachment member 46 located on each lateral side of housing 22. A head strap may be adjustably attached to each headgear attachment member 46 to help secure mask apparatus 16 against the patient's head.

Housing 22 may be a single, integrated component, or may include multiple components coupled together.

Cushion 20 may be directly or indirectly coupled to housing 22. In some embodiments, cushion 20 is releasably coupled to housing 22 such that cushion 20 may be removed from, and reattached to, housing 22. Cushion 20 may be releasably coupled to housing 22, directly or indirectly, in any suitable manner. For example, cushion 20 may be releasably coupled to housing 22 in any manner disclosed in co-pending U.S. patent application Ser. No. 11/469,260, filed Aug. 31, 2006, and entitled "Patient Interface Assembly for a Breathing Assistance System," which is hereby incorporated by reference. As another example, cushion 20 may be releasably coupled to housing 22 using any suitable clips or other connectors.

Gas delivery conduit 24 may comprise any one or more conduits configured to communicate gas from gas delivery system 14 toward cushion 20. Such conduits may include, e.g., one or more flexible hoses and/or rigid conduits. Gas delivery conduit 24 may be coupled at a first end to connection system 18 (e.g., a breathing circuit), and may be directly or indirectly coupled at a second end to housing 22 and/or cushion 20 in order to deliver gas to patient 12 via cushion 20. In the embodiment shown in FIG. 1, gas delivery conduit 24 is removably coupled to ball joint 26. As discussed below, ball member 36 includes an opening extending therethrough such that gas may be delivered from gas delivery conduit 24, through the opening in ball member 36, through housing 22 and cushion 20, and to patient 12.

In some embodiments, gas delivery conduit 24 may be secured to the patient's head. For example, as shown in FIG. 1, gas delivery conduit 24 may be extend upwardly in front of the patient's head and may be releasably secured to headgear 30 near the top of the patient's head.

Ball joint 26 may be configured to provide a flexible, movable, and/or adjustable connection between gas delivery conduit 24 and housing 22. In some embodiments, ball joint 26 may provide for multi-axial rotation of gas delivery conduit 24 relative to housing 22. In the illustrated embodiment, ball joint 26 includes ball member 36 positioned in opening 34 formed in housing 22. Ball member 36 may be secured against housing 22 may a mounting system 50 (discussed below with reference to FIG. 2). Together, ball member 36, housing 22, and mounting system 50 may form ball joint 26.

Gas exhaust system 28 may be configured to remove exhaled gas away from patient 12. In the illustrated embodiments, gas exhaust system 28 includes one or more exhaust passageways 38 defined between opening 34 of housing 22 and an outer surface of ball member 36. Such exhaust passageways 38 may be configured to communicate exhaust gas from patient 12 (e.g., $CO_2$) away from patient 12. In some embodiments, opening 34 may define a perimeter including one or more contact portions alternative with one or more non-contact portions. The non-contact portions may be portions of the perimeter of opening 34 that do not contact ball member 36, thus defining an exhaust passageway 38 between ball member 36 and opening 34. Gas exhaust system 28 is discussed in greater detail below with reference to FIGS. 6A-6B.

Headgear 30 may be configured to secure mask apparatus 16 on the patient's head and/or to secure cushion 20 against the patient's face. Headgear 30 may include any one or more components. For example, headgear 30 may include a head strap 60 including multiple strap portions 62 coupled to mask apparatus 16 at various locations. In the illustrated embodiment, head strap 60 includes: (a) a left side strap portion 62a extending around the left side of the patient's face and secured to a left headgear attachment member 46a, (b) a right side strap portion 62b extending around the right side of the patient's face and secured to a right headgear attachment member 46b, and (c) a top strap portion 62c extending over the top of the patient's head and secured to a free end of adjustment arm 40.

Strap portions 62 may be coupled to mask apparatus 16 in any suitable manner. For example, as shown in FIG. 1, each strap portion 62 may be threaded through an opening formed in a component of mask apparatus 16, and folded back and attached to itself using hook and loop fasteners. Thus, each strap portion 62 may me adjustable as desired by patient 12.

Each strap portion 62 may be integrated with or coupled to other strap portions 62 in any suitable manner, e.g., using hook and loop fasteners or other connection devices. In one embodiment, strap portions 62a, 62b, and 62c are integrated in a single piece head strap 60. Strap portions 62 may be formed from any one or more flexible and/or elastic materials. For example, strap portions 62 may be formed from elastomeric materials, neoprene, fabric, or other similar materials.

Adjustment system 32 may be configured for adjusting the fit of mask apparatus 16 against the patient's head (e.g., for adjusting the fit of cushion 20 against the patient's face). As discussed above, adjustment system 32 may include an adjustment arm 40 and a locking member 42 supported by housing 22. At least one of adjustment arm 40 and a locking member 42 may be configured for attachment to headgear 30, and may be adjusted relative to housing 22 in order to adjust the fit of mask apparatus 16 against the patient's head. For example, as discussed below with reference to FIGS. 7A-7B, adjustment arm 40 may be rotatably coupled to housing 22 such that adjustment arm 40 may rotate as indicated by arrow 66, in order to adjust the distance between a free end of adjustment arm 40 and the patient's head. Locking member 42 may interact with adjustment arm 40 in order to lock adjustment arm 40 in one of a plurality of rotational positions.

As discussed above, adjustment system 32 may be used for adjusting the fit of mask apparatus 16 against the patient's head. For example, mask apparatus 16 may be adjusted using adjustment system 32 in order to properly secure mask apparatus 16 onto the patient's head, and/or to provide a proper seal between cushion 20 and the patient's face. In this manner, adjustment system 32 may be used to adjust mask apparatus 16 to fit a variety of patient's having various head or face shapes and/or sizes. For example, mask apparatus 16 may be adjusted to fit both children and adults.

Figure 2:
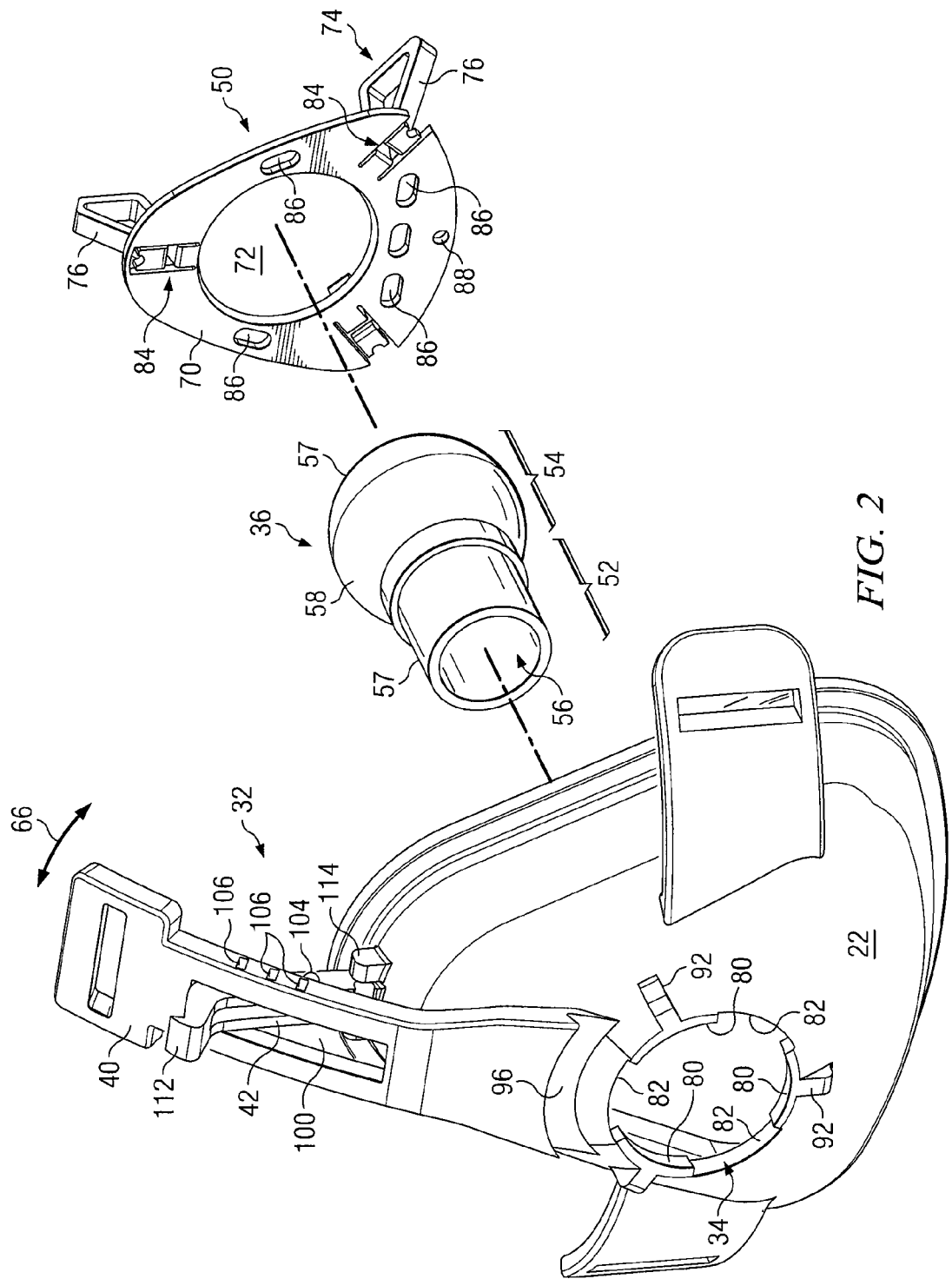
FIG. 2 illustrates an exploded view of a portion of mask apparatus, indicating the assembly of a housing, a ball member, and a mounting system to form a ball joint, according to one embodiment of the disclosure.

FIG. 2 illustrates an exploded view of a portion of mask apparatus, indicating the assembly of housing 22, ball member 36, and mounting system 50 to form ball joint 26, according to one embodiment of the disclosure. Ball member 36 may be inserted through an opening 34 formed in housing 22. Mounting system 50 may be configured to secure ball member 36 in housing opening 34 such that housing 34, ball member 36, and mounting system 50 form ball joint 26 allowing ball member 36 to rotate relative to the housing 22 and mounting system 50.

Ball member 36 may include a cylindrical portion 52 configured to be coupled to gas delivery conduit 24 and a spherical portion 54 positioned in opening 34 in housing 22. Ball member 36 may include an opening 56 extending therethrough such that when mask apparatus is assembled and secured to patient 12, gas may be delivered from gas delivery conduit 24, through opening 56, through housing 22 and cushion 20, and to patient 12. Ball member 36 may be a single integrated component, or may include multiple components coupled together in any suitable manner. For example, in one embodiment, ball member 36 includes (a) a body portion 57 that defines cylindrical portion 52 and opening 56, and (b) a hemispherical cap portion 58 that slides over cylindrical portion 52 and cooperates with a hemispherical portion of body portion 57 to define spherical portion 54.

Mounting system 50 may comprise any one or more mounting members configured to secure ball member 36 in housing opening 34. One or more of such mounting members may be directly or indirectly coupled to housing 22. In addition, such one or more mounting members may define an opening into which a portion of ball member 36 may be positioned.

In the illustrated embodiment, mounting system 50 comprises a mounting plate 70 including a mounting plate opening 72. Once mounting plate 70 is assembled with housing 22, a first, front portion of ball member 36 may extend through housing opening 34 and a second, rear portion of ball member 36 may extend through mounting plate opening 34.

Mounting system 50 may be releasably attached to housing 22 such that ball joint 26 may be assembled and disassembled, and such that ball member 36 may be removed from housing opening 34. Mounting system 50 may be releasably attached to housing 22 in any suitable manner. In some embodiments, mounting system 50 may include a securing system 74 for releasably securing mounting system 50 to housing 22. For example, in the illustrated embodiment, mounting plate 70 may include one or more securing members 76 configured for releasable attachment to housing 22. As discussed below with reference to FIGS. 4A-4C, securing members 76 may be manually moved from a first position for securing mounting plate 70 to housing 20 and a second position for releasing mounting plate 70 from housing 22.

As discussed above, gas exhaust system 28 may include one or more exhaust passageways 38 defined between housing opening 34 and an outer surface of ball member 36 for communicating exhaust gas away from patient 12. As shown in FIG. 2, opening 34 may define a perimeter including one or more contact portions 80 alternating with one or more non-contact portions 82. Contact portions 82 generally contact ball member 36 when ball joint 26 is assembled. Non-contact portions 82 generally do not contact ball member 36, thus defining exhaust passageways 38 between ball member 36 and opening 34. In this embodiment, three contact portions 82 are alternated with three non-contact portions 82, thus defining three exhaust passageways 38. In other embodiments, mask apparatus 16 may include any other number and/or configuration of contact portions 82, non-contact portions 82, and/or exhaust passageways 38.

As shown in FIG. 2, each non-contact portion 82 may be a cut-away or receded portion from the perimeter of opening 34. Each contact portion 80 and/or non-contact portion 82 may have any suitable size, shape, and/or configuration. For example, contact portions 80 and/or non-contact portions 82 may be sized, shaped, and/or configured to form exhaust passageways 38 that allow a particular flow rate of exhaust gas through such passageways 38. As another example, contact portions 80 and/or non-contact portions 82 may be sized, shaped, and/or configured to form exhaust passageways 38 that direct exhaust gasses in one or more particular direction.

Mounting system 50 may define one or more pathways for exhaust gas to be communicated from patient 12 to exhaust passageways 28. In the illustrated embodiment, mounting plate 70 may include or define one or more openings allowing exhaust gas from patient 12 to pass through toward exhaust passageways 28. For example, mounting plate 70 may be shaped and/or sized to define one or more passages between the outer perimeter of mounting plate 70 and an inner surface of housing 22. As another example, mounting plate 70 may define one or more passages allowing exhaust gas to pass through toward exhaust passageways 28. In the illustrated embodiment, each securing member 76 defines an opening 84 allowing exhaust gas to pass through toward exhaust passageways 28. As another example, mounting plate 70 may include one or more openings 86 allowing exhaust gas to pass through toward exhaust passageways 28.

Mounting system 50 may also include one or more alignment devices for aligning mounting system 50 with housing 22. In this embodiment, mounting plate 70 includes one or more alignment holes 88 configured to receive one or more alignment members for aligning mounting plate 70 with housing 22, as discussed below with reference to FIG. 3.

One or more stiffening members 92 may disposed proximate the housing opening 34 for providing structural integrity around opening 34 (e.g., to resist deformation of housing opening 34). Stiffening members 92 may be integrated with or coupled to housing 22 in any suitable manner. In the illustrated embodiment, housing 22 includes an integrated stiffening member 92 proximate each contact portion 80 for providing structural integrity around opening 34.

Gas exhaust system 28 is further discussed below with reference to FIGS. 6A-6B.

FIG. 2 also illustrates adjustment system 32 for adjusting the fit of mask apparatus 16 against the patient's head (e.g., for adjusting the fit of cushion 20 against the patient's face). Adjustment arm 40 and locking member 42 may be coupled to housing 22. In some embodiments, adjustment arm 40 and/or locking member 42 are formed integral with housing 22. For example, in the illustrated embodiment, adjustment arm 40 is integrally coupled to housing 22 by a living hinge, which allows adjustment arm 40 to rotate relative to housing 22 in the direction indicated by arrow 66. In addition, locking member 42 may be integrally coupled to housing 22 by a living hinge or a less flexible joint that allows some flexing of locking member 42 relative to housing 22, but less than that of adjustment arm 40.

Adjustment arm 40 and locking member 42 may interact with adjustment arm 40 in any suitable manner to allow adjustment arm 40 to be releasably locked in a plurality of different positions. In the illustrated embodiment, adjustment arm 40 includes a slot 100 configured to receive locking member 42. Locking member 42 may slide through slot 100 as adjustment arm 40 rotates along path 66.

Locking member 42 may include one or more first locking elements 104, and adjustment arm 40 may include one or more second locking elements 106 configured to interact with first locking elements 104 to releasably secure adjustment arm 40 in one of multiple different predetermined rotational positions. Locking elements 104 and 106 are better illustrated in FIGS. 5 and 7A-7D, which are discussed in greater detail below.

Locking elements 104 and 106 may include any elements configured to interact to releasably couple adjustment arm 40 and locking member 42. For example, locking elements 104 and/or 106 may comprise any suitable projections, bumps, teeth, indentations, holes, grooves, clips, hooks, latches, or any other suitable members or devices.

In the illustrated embodiment, locking member include three projections (e.g., bumps) 104 and adjustment arm 40 includes three indentations or openings 106. Each indentation 106 is configured to receive a corresponding projection 104 to lock adjustment arm 40 in a particular rotational position. Thus, adjustment arm 40 may be releasably locked in three predetermined rotational positions. In some embodiments, adjustment arm 40 may be manually moved between the three locking positions, which may include manual manipulation of adjustment arm 40 and/or locking member 42. For example, in one embodiment, if adjustment arm 40 is locked in a first position in which a first projection 104 is secured in a first indentation 106, adjustment arm 40 and locking member 42 may be flexed laterally in opposite directions to release the first projection 104 from the first indentation 106. Adjustment arm 40 may then be rotated along path 66 until a second projection 104 is received in a second indentation 106 to lock adjustment arm 40 in a second rotational position.

Adjustment system 32 may also include one or more stop elements 110 to limit the rotation of adjustment arm 40 in one or more directions. In the illustrated embodiment, locking member 42 includes a hook portion that acts as a first stop 112 to limit the rotation of adjustment arm 40 in a direction away from the patient's face. A second stop 114 may be located proximate the base of locking member 42 to limit the rotation of adjustment arm 40 in a direction toward the patient's face.

Figure 3:
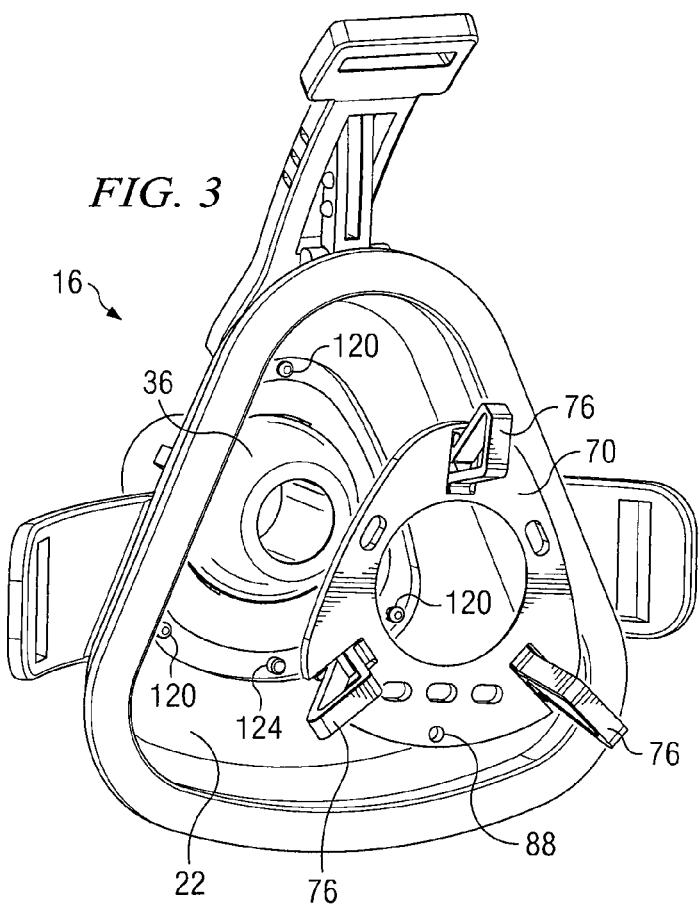
FIG. 3 illustrates an example mask apparatus with a mounting plate aligned for attachment to a housing, according to one embodiment of the disclosure.

FIG. 3 illustrates mask apparatus 16, with mounting plate 70 aligned for attachment to housing 22, according to one embodiment of the disclosure. In this illustration, ball member 36 has been inserted in housing opening 34, and mounting plate 70 may be coupled to housing 22 to secure ball member 36 between housing 22 and mounting plate 70 to form ball join 26.

In this embodiment, mounting plate 70 has a substantially triangular shape and includes three securing members 76 positioned around the perimeter of plate 70. Each securing member 76 may be configured to be releasably coupled to a corresponding attachment member 120 for coupling plate 70 to housing 22. In this embodiment, three attachment members 120 are formed integral with, or coupled to, an inner surface of housing 22. As discussed with reference to FIGS. 4A-4C, each securing member 76 may comprise a flexible arm or clip that may be manually flexed between a first position for attaching that securing member 76 to the corresponding attachment member 120 and a second position for releasing the securing member 76 from the attachment member 120.

In addition, one or more alignment members 124 may be provided for aligning mounting plate 70 with housing 22. In this embodiment, an alignment member 124 is configured to fit within an alignment hole 88 formed in mounting plate 70 in order to align mounting plate 70 with housing 22.

Figure 4A:
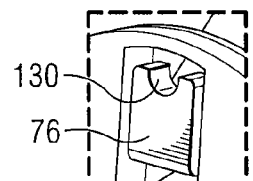
FIGS. 4A-4C illustrates a detailed view of an example securing member and corresponding attachment member for securing a mounting plate to a housing, according to one embodiment of the disclosure.
Figure 4B:
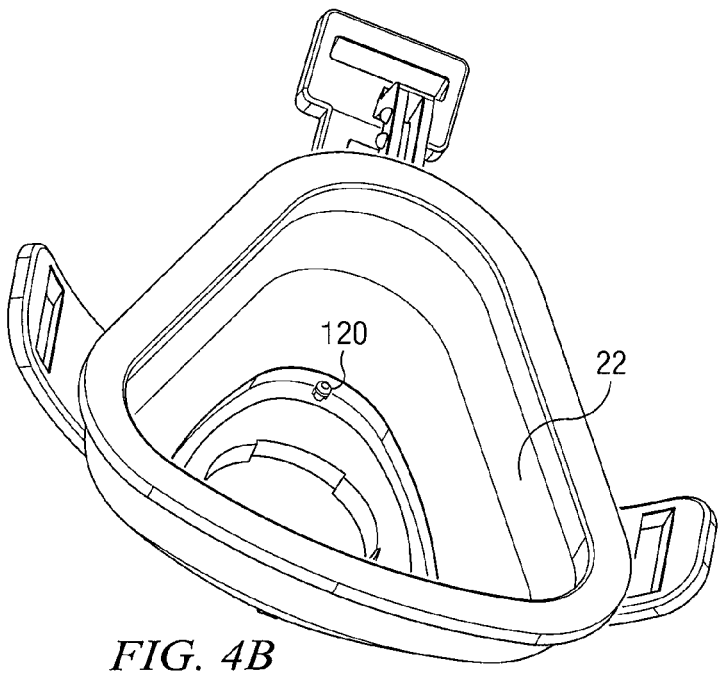
Figure 4C:
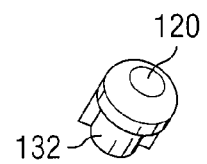

FIGS. 4A-4C illustrates a detailed view of an example securing member 76 and corresponding attachment member 120 for securing mounting plate 70 to housing 22, according to one embodiment of the disclosure. Securing member 76 may comprise a flexible arm or clip that may be manually flexed to attach or detach securing member 76 from attachment member 120. In this embodiment, securing member 76 includes a forked, or arced, end portion 130 that may be configured to interlock with (e.g., snap into) attachment member 120. Attachment member 120 may comprise a peg or other element having an undercut boss region 132 configured to receive forked end portion 130 of securing member 76. To attach mounting plate 70 to housing 22, securing members 76 may be flexed to move end portions 130 inwardly toward the center of mounting plate 70, plate 70 may then be aligned (e.g., using alignment member 124 and alignment hole 88) and pressed against housing 22, and securing members 76 may then be released such that end portions 130 of securing members 76 interlock with undercut boss region 132 of attachment members 120. It should be understood that any other suitable members or devices may be used for releasably attaching mounting plate 70 to housing 22.

Figure 5:
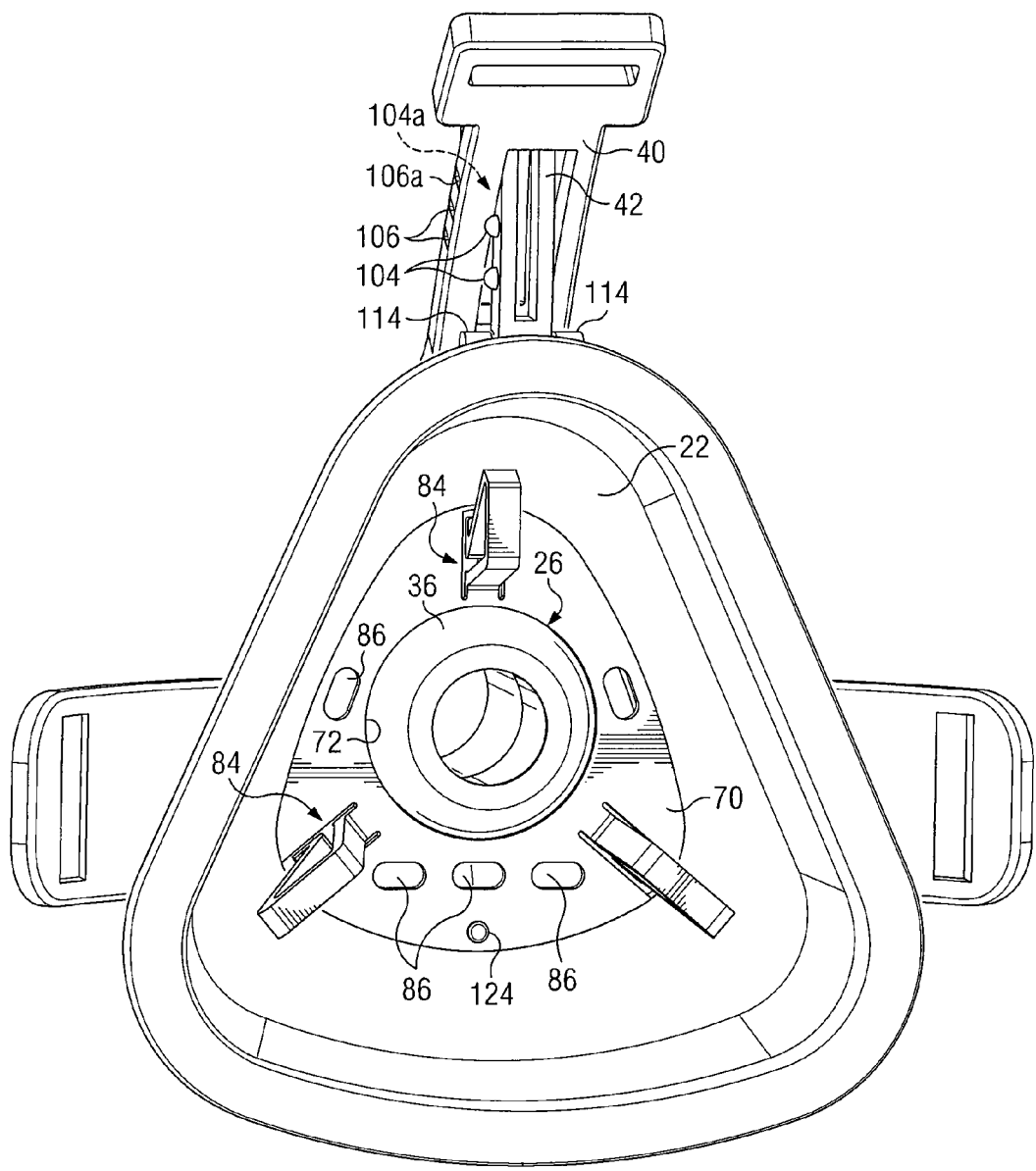
FIG. 5 illustrates the inside of a mask apparatus with a mounting plate secured to a housing, forming a ball joint, according to one embodiment of the disclosure.

FIG. 5 illustrates the inside of mask apparatus 16 with mounting plate 70 secured to housing 22, thus forming ball joint 26, according to one embodiment of the disclosure. A rear portion of ball member 36 may extend into and/or through opening 72 formed in mounting plate 70. As discussed above, openings 86 in mounting plate 70 may provide passageways for exhaust gas to pass from patient 12 to exhaust passageways 28 (shown in FIGS. 2 and 6A-6B).

FIG. 5 also illustrates adjustment arm 40 releasably locked with locking member 42. As discussed above, in this embodiment, locking member 42 includes three projection 104 configured to lock with three indentations 106 formed in adjustment arm 40. In this illustration, a first projection (not shown) is received in a first indentation 106a to releasably secure adjustment arm 40 in a first of three predetermined rotational positions. FIG. 5 also illustrates second stop 114 (discussed above regarding FIG. 2) located proximate the base of locking member 42 for limiting the rotation of adjustment arm 40 in a direction toward the patient's face.

Figure 6B:
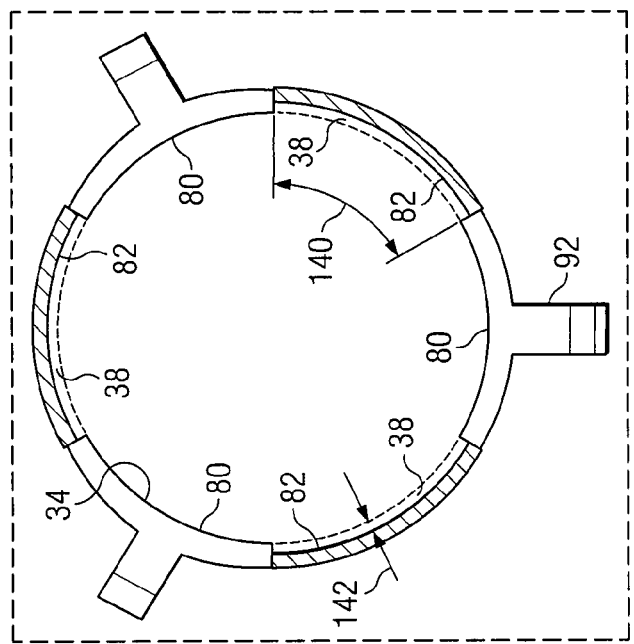
FIGS. 6A-6B illustrate a gas exhaust system for removing exhaled gas away from a patient, according to one embodiment of the disclosure.
Figure 6A:
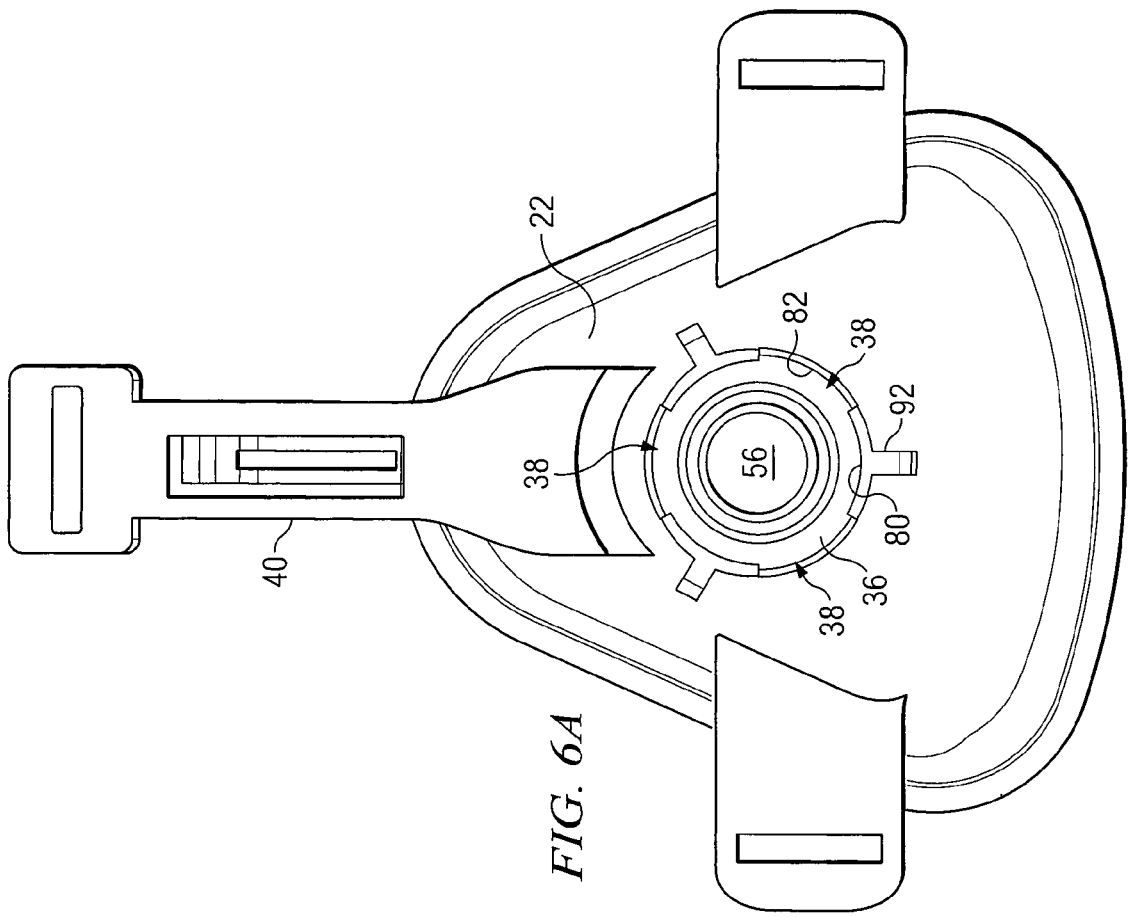

FIGS. 6A-6B illustrate gas exhaust system 28 for removing exhaled gas away from patient 12, according to one embodiment of the disclosure. As discussed above, gas exhaust system 28 may include one or more exhaust passageways 38 defined between housing opening 34 and an outer surface of ball member 36 for communicating exhaust gas away from patient 12. In some embodiments, opening 34 may define a perimeter including one or more contact portions 80 alternating with one or more non-contact portions 82. Contact portions 82 generally contact ball member 36 when ball joint 26 is assembled. Non-contact portions 82 generally do not contact ball member 36, thus defining exhaust passageways 38 between ball member 36 and opening 34. In this embodiment, three contact portions 82 are alternated with three non-contact portions 82, thus defining three exhaust passageways 38. In other embodiments, mask apparatus 16 may include any other number and/or configuration of contact portions 82, non-contact portions 82, and/or exhaust passageways 38.

As shown in FIGS. 6A-6B, each non-contact portion 82 may be a cut-away or receded portion from the perimeter of opening 34. Each contact portion 80 and/or non-contact portion 82 may have any suitable size, shape, and/or configuration, e.g., to form exhaust passageways 38 having desired shapes, sizes, and/or configurations. For example, a width 140 and depth 142 of each non-contact portion 82 may be selected for defining exhaust passageways 38 that (a) allow a particular flow rate of exhaust gas through passageways 38, (b) provide for particular sound characteristics for gasses flowing through passageways 38, and/or (c) direct exhaust gasses in one or more particular direction.

For example, width 140 and depth 142 of each non-contact portion 82 may be sized to provide a total gas passageway area of about 0.13-0.25 $cm^2$. As another example, width 140 and depth 142 of each non-contact portion 82 may be sized to provide a gas flow of about 10-40 liter/min at 10 cm $H_2O$. In some embodiments, width 140 and depth 142 of each non-contact portion 82 may be sized to provide a gas flow of about 15-25 liter/min at 10 cm $H_2O$. In one example embodiment, each non-contact portion 82 has a width 140 of about 0.5 inch and a depth 142 of about 0.015 inch.

FIGS. 7A-7D illustrate the operation of adjustment system 32 for adjusting the fit of mask apparatus 16 against the patient's head (e.g., for adjusting the fit of cushion 20 against the patient's face), according to one embodiment of the disclosure. As discussed above, adjustment arm 40 may be rotatably coupled to housing 22 such that adjustment arm 40 may rotate as indicated by arrow 66, in order to adjust the distance between a free end 150 of adjustment arm 40 and the patient's head. Adjustment arm 40 and locking member 42 may interact with adjustment arm 40 in any suitable manner to allow adjustment arm 40 to be releasably locked in a plurality of different positions. In the illustrated embodiment, locking member 42 slides through slot 100 formed in adjustment arm 40.

In this embodiment, locking member 42 includes three locking elements 104, and adjustment arm 40 includes three locking elements 106 configured to interact with locking elements 104 to releasably secure adjustment arm 40 in three predetermined rotational positions. In addition, adjustment system 32 may include one or more stop elements 110 to limit the rotation of adjustment arm 40 in one or more directions. In the illustrated embodiment, locking member 42 includes a first stop 112 (e.g., a hook portion) to limit the rotation of adjustment arm 40 in a first direction indicated by arrow 152, and a second stop 114 proximate the base of locking member 42 to limit the rotation of adjustment arm 40 in a second direction indicated by arrow 154.

Figure 7A:
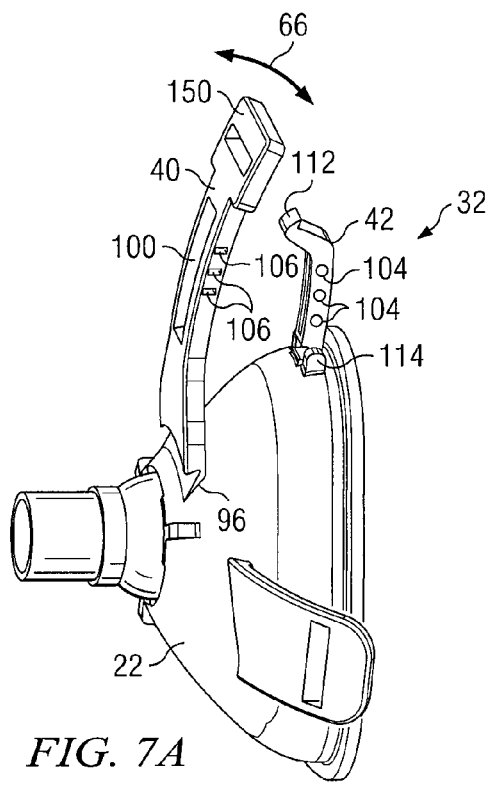
FIGS. 7A-7D illustrate the operation of an adjustment system for adjusting the fit of a mask apparatus against a patient's head (e.g., for adjusting the fit of a mask cushion against the patient's face), according to one embodiment of the disclosure.

FIG. 7A illustrates adjustment arm 40 free from locking arm 40.

Figure 7B:
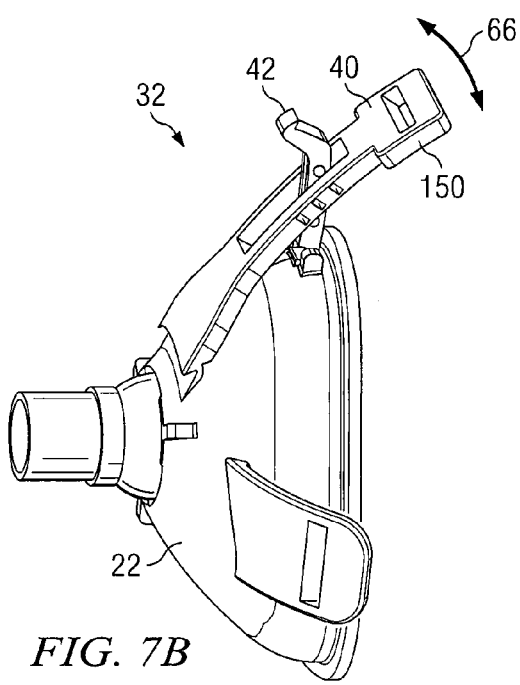
Figure 7C:
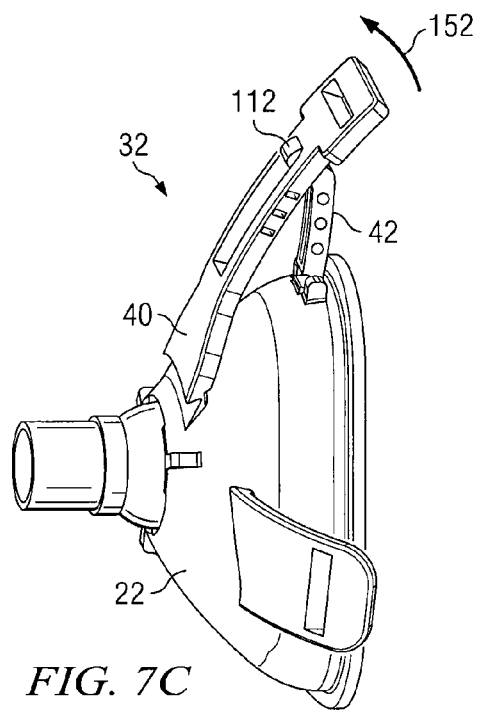
Figure 7D:
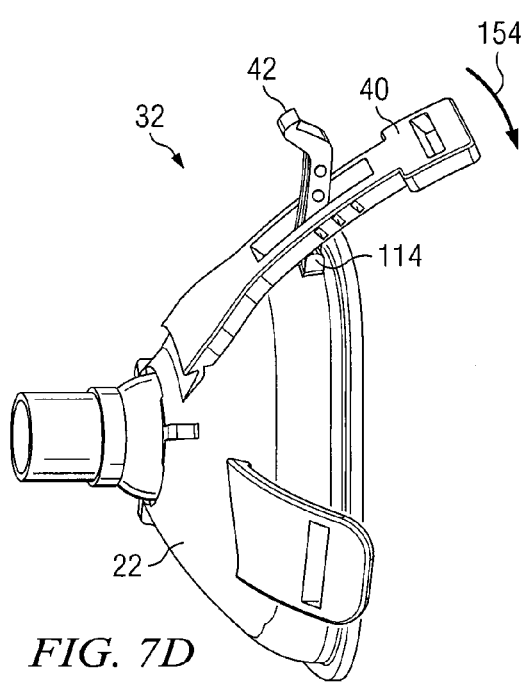

FIGS. 7B-7D interacting with locking arm 40. To move adjustment arm 40 from the position shown in FIG. 7A to any of the positions shown in FIGS. 7B-7D, locking member 42 may be inserted through slot 100 formed in adjustment arm 40. In one embodiment, in order to position locking member 42 within slot 100, a user may flex locking member 42 slightly toward adjustment arm 40 such that the free end of locking member 42 fits within slot 100. Adjustment arm 40 may then be rotated along path 66 between the multiple different locking positions. To release adjustment arm 40 from locking member 42 (i.e., to return adjustment arm 40 to the position shown in FIG. 7A), the user may again flex locking member 42 slightly toward adjustment arm 40 such that the free end of locking member 42 may be removed from slot 100.

As shown in FIGS. 7B-7D, adjustment arm 40 may be secured in any of the three predetermined rotational positions using locking elements 104 and 106, positioned against first stop 112, or positioned against second stop 114. In particular, FIG. 7B illustrates adjustment arm 40 locked in a middle locking position; FIG. 7C illustrates adjustment arm 40 positioned against first stop 112; and FIG. 7D illustrates adjustment arm 40 positioned against second stop 114. Adjustment arm 40 may be manually moved between the three locking positions and two stop positions. As discussed above, in one embodiment, in order to move adjustment arm 40 may be manually moved between the three locking positions, adjustment arm 40 and locking member 42 may be flexed laterally in opposite directions to release a particular projection 104 from a corresponding indentation 106. Adjustment arm 40 may then be rotated along path 66 until another projection 104 is received in another indentation 106 to lock adjustment arm 40 in a different rotational position.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed:

1. A mask apparatus for use in a breathing assistance system, the mask apparatus comprising:
    a housing configured to support a cushion configured to provide a seal against a patient's face, the housing having a first side and a second side, the first side defining a first housing opening, and the second side configured to face the cushion and defining a second housing opening, the housing defining one or more housing exhaust passageways;
    a ball member positioned in the first housing opening, the ball member having a ball member opening defining a gas delivery passageway for communicating gas though the first housing opening; and
    a mounting system configured to secure the ball member in the first housing opening such that the housing, the ball member, and the mounting system define a ball joint allowing the ball member to rotate about multiple axes relative to the housing and the mounting system;

wherein the mounting system includes one or more securing elements configured to be manually moved between a first position for securing the mounting system to the housing and a second position for releasing the mounting system from the housing;

wherein the mounting system includes one or more mounting system exhaust passageways configured to cooperate with the one or more housing exhaust passageways for communicating exhaust gas away from the patient, the one or more housing exhaust passageways being separate from the gas delivery passageway defined by the ball member opening.

2. A mask apparatus according to claim 1, wherein:
the mounting system is coupled to the housing and defines a mounting system opening; and
a first portion of the ball member extends into the first housing opening and a second portion of the ball member extends into the mounting system opening.

3. A mask apparatus according to claim 2, wherein the mounting system comprises a mounting plate defining the mounting system opening.

4. A mask apparatus according to claim 2, wherein the mounting system comprises multiple mounting members defining the mounting system opening.

5. A mask apparatus according to claim 1, wherein the mounting system is releasably coupled to the housing such that the ball may be removed from the first housing opening.

6. A mask apparatus according to claim 1, wherein the one or more exhaust passageways are defined between an outer surface of the ball member and the first housing opening, the one or more exhaust passageways configured for communicating exhaust gas away from the patient.

7. A mask apparatus according to claim 6, wherein:
the first housing opening defines a perimeter including one or more contact portions and one or more non-contact portions alternating around the perimeter;
the one or more contact portions are configured to contact the ball member; and
the one or more non-contact portions at least partially define the one or more exhaust passageways.

8. A mask apparatus according to claim 1, wherein the housing includes one or more stiffening members disposed proximate the first housing opening for resisting deformation of the first housing opening.

9. A mask apparatus according to claim 1, wherein the ball member includes a body portion that defines the ball member opening and a hemispherical cap portion coupled to the body portion.

10. A mask apparatus according to claim 1, wherein the ball member includes a cylindrical portion and a spherical portion, the cylindrical portion configured to be coupled to a gas delivery conduit, and the spherical portion configured to be positioned in the first housing opening.

11. A mask apparatus according to claim 1, wherein:
the ball member includes a first end configured to be coupled to a gas delivery conduit; and
the ball member opening is configured to deliver gas from the gas delivery conduit toward the patient.

12. A mask apparatus according to claim 1, wherein the ball member opening has a smaller diameter than the first housing opening.

13. A mask apparatus according to claim 1, further comprising a headgear for securing the mask apparatus to the patient's head.

14. A mask apparatus according to claim 1, wherein one or more components are coupled between the housing and the cushion such that the cushion is indirectly coupled to the housing.

15. A breathing assistance system, comprising:
a gas delivery apparatus configured to deliver gas toward a patient;
a mask apparatus in fluid communication with the gas delivery apparatus, the mask apparatus including:
a housing configured to support a cushion configured to provide a seal against the patient's face, the housing defining an inner side facing the patient when the mask apparatus is worn by the patient, an outer side facing away from the patient, and a first housing opening;
a ball member positioned in the first housing opening, the ball member having a ball member opening defining a gas delivery passageway for communicating gas though the first housing opening, wherein one or more exhaust passageways are defined between a surface of the housing opening and the ball member such that the one or more exhaust passageways are separate from the gas delivery passageway defined by the ball member opening; and
a mounting system operatively coupled to the inner side of the housing facing the patient, the mounting system configured to secure the ball member in the first housing opening and substantially between the mounting system and the housing such that the housing, the ball member, and the mounting system define a ball joint allowing the ball member to rotate about multiple axes relative to the housing and the mounting system, the mounting system defining one or more openings for communicating exhaust gas away from the patient and toward the one or more exhaust passageways defined between the surface of the housing opening and the ball member; and
a connection system configured to communicate gas from the gas delivery apparatus to the mask apparatus.

16. A mask apparatus for use in a breathing assistance system, comprising:
a ball member secured between a mounting system and a housing configured to support a cushion for providing a seal against a patient's face, the ball member secured in a housing opening defined in the housing;
wherein the mounting system is operatively coupled to an inner side of the housing facing the patient when a mask apparatus is worn by the patient;
wherein the ball member is configured to rotate about multiple axes relative to the housing and the mounting system;
wherein the ball member has a ball member opening defining a gas delivery passageway for communicating gas from a gas delivery conduit toward the patient though the first housing opening;
wherein the mounting system and the housing each define one or more exhaust passageways separate from the gas delivery passageway defined by the ball member opening; and
wherein the mounting system includes one or more securing elements configured to be manually moved between (a) a first position for securing the mounting system to the housing and (b) a second position for releasing the mounting system from the housing.

17. A method for assembling a mask apparatus for use in a breathing assistance system, the method comprising:
positioning a ball member in a housing opening defined in a housing configured to support a cushion for providing a seal against a patient's face, the ball member having a ball member opening defining a gas delivery passageway for communicating gas though the housing opening; and attaching a mounting system to the housing to secure the ball member in the housing opening by manually securing one or more mounting system securing elements the housing such that the housing, the ball member, and the mounting system define a ball joint allowing the ball member to rotate about multiple axes relative to the housing and the mounting system, and wherein the mounting system and the housing each define one or more exhaust passageways separate from the gas delivery passageway defined by the ball member opening.

18. A method according to claim 17, further comprising:
attaching the cushion to the housing;
attaching the ball member to a gas delivery conduit;
securing the mask apparatus to the patient's head using a headgear; and
delivering gas to the patient such that gas is communicated through the gas delivery conduit, through the ball member opening, and to the patient.

19. A mask apparatus for use in a breathing assistance system, the mask apparatus comprising:

housing means for supporting a cushion configured to provide a seal against a patient's face, the housing means defining an inner side facing the patient when the mask apparatus is worn by the patient, an outer side facing away from the patient, and a first housing opening;

ball means positioned in the first housing means opening, the ball means having a ball means opening defining a gas delivery passageway for communicating gas though the first housing means opening, wherein one or more exhaust passageways are defined between a surface of the housing opening and the ball means such that the one or more exhaust passageways are separate from the gas delivery passageway defined by the ball means opening; and mounting means operatively coupled to the inner side of the housing means facing the patient, the mounting means configured for securing the ball means in the first housing means opening and substantially between the mounting means and the housing means such that the housing means, the ball means, and the mounting means define a ball joint allowing the ball means to rotate about multiple axes relative to the housing means and the mounting means, the mounting means defining one or more openings for communicating exhaust gas away from the patient and toward the one or more exhaust passageways defined between the surface of the housing opening and the ball means.

* * * * *